United States Patent [19]

Nalowaniec et al.

[11] Patent Number: 5,013,382
[45] Date of Patent: May 7, 1991

[54] METHOD OF MAKING AN ABSORBENT DISPOSABLE ARTICLE

[75] Inventors: Krzysztof Nalowaniec; Kurt Simmler, both of Heidenheim, Fed. Rep. of Germany

[73] Assignee: Paul Hartmann Aktiengesellschaft, Heidenheim, Fed. Rep. of Germany

[21] Appl. No.: 177,898

[22] Filed: Mar. 31, 1988

Related U.S. Application Data

[62] Division of Ser. No. 38,546, Apr. 15, 1987.

[30] Foreign Application Priority Data

Apr. 17, 1986 [DE] Fed. Rep. of Germany ....... 3613042

[51] Int. Cl.$^5$ .................. B32B 31/08; B32B 31/10
[52] U.S. Cl. .................................. 156/298; 156/301; 156/302; 156/324; 604/378
[58] Field of Search ............... 156/164, 566, 301, 292, 156/291, 298, 299, 300, 302, 324; 604/365, 381, 378, 366; 427/209, 211

[56] References Cited

U.S. PATENT DOCUMENTS

| | | | |
|---|---|---|---|
| 3,604,422 | 9/1971 | Sabee | 604/365 |
| 3,779,246 | 12/1973 | Mesek et al. | 604/366 |
| 3,799,167 | 3/1974 | Miller et al. | 604/372 |
| 3,840,418 | 10/1974 | Sabee | 156/244.25 |
| 3,945,386 | 3/1976 | Anczurowski et al. | 128/287 |
| 4,069,822 | 1/1978 | Buell | 156/91 X |
| 4,107,426 | 8/1978 | Gordon | 604/381 |
| 4,573,986 | 3/1986 | Minetola et al. | 156/276 X |
| 4,849,049 | 7/1989 | Colton | 156/291 |

Primary Examiner—Michael W. Ball
Assistant Examiner—Michele K. Yoder
Attorney, Agent, or Firm—Dick and Harris

[57] ABSTRACT

In an absorbent disposable article, such as in particular a diaper, in which an absorbent body is covered on one side by a liquid-impermeable protective sheet and on the opposite side by a porous layer, certain edge areas of the porous cover layer should be provided with a liquid-impermeable protective layer.

This protective layer is formed as a prefabricated impervious sheet and possesses, before being placed on cover layer, on one side a smooth and the other side an extremely coarse surface. The impervious sheet serving as the protective layer penetrates essentially exclusively with its coarse surface areas inside the cover layer. Through the smooth side of this impervious sheet, an absolute imperviousness is assured. Because of the physical bond, which forms between the impervious sheet and the cover layer, the impervious sheet can be formed extremely thin, i.e., a minimum amount of material is sufficient for the impervious sheet.

For only partial penetration of the impervious sheet into the cover layer, special manufacturing processes are indicated.

10 Claims, 3 Drawing Sheets

METHOD OF MAKING AN ABSORBENT DISPOSABLE ARTICLE

This application is a continuation, division of application Ser. No. 7/038,546, filed Apr. 15, 1987.

BACKGROUND OF THE INVENTION

The invention concerns an absorbent disposable article, such as in a particular a diaper including, in part, an absorbent body having a liquid-permeable protective sheet on one side and a porous cover layer on an opposite side.

Such articles are known, for example, from German published Patent Application No. 19 14 179 and European Patent No. 00 59 015 81.

In both cases, individual sheets are laid up as barrier layers, which either are bonded only on the edge of the disposable article to the porous cover layer (GPPA 19 14 179) or, for edge reinforcement, are also additionally bonded to the cover layer at further locations disposed, respectively, at a distance from one another, distributed over the entire surface of the barrier layer (EP 0 059 015 B1).

The drawback of these barrier layers consists in that they represent inprinciple in each case an independent layer, which is bonded to the cover layer solely in individual spots. Because of that, these barrier layers must exhibit, i.e., a thickness which imparts to them an independently sufficient strength. Therefore, these barrier layers require a relatively large amount of material. In the case of the class of mass-produced articles, this already is of consequence from the standpoint of cost. Also, those layers are unpleasantly stiff in wear.

It is, moreover, already known from U.S. Pat. No. 3,799,167 to produce the corresponding barrier layers at the edge of an absorbent disposable article through impregnation of the porous cover layer with a liquid-impermeable material. The shortcoming of this embodiment consists in that again a relatively higher expenditure of material is required in order to achieve an assured imperviousness of the layer by complete filling of the pores of the cover layer. As a result of the complete penetration into the pores in the course of impregnation of the liquid-impermeable filler materials, the cover layer is quite hard and relatively stiff. In the cases where the disposable article to be produced comes with the cover layer in contact with the skin of the person wearing the disposable article on his or her body, this is perceived as unpleasant; then, in the case of disposable articles to be worn on the body, a porous cover layer directly adjacent the skin is made from a soft, pleasant to wear material. These pleasant to wear properties, naturally, are not possessed by a liquid-impermeable filler material.

In the case of a further absorbent disposable article, known from U.S. Pat. No. 3,604,422, a liquid-impermeable coating can, i.e., be applied to the porous cover layer. When, on the other hand, applying such a coating, as again according to U.S. Pat. No. 3,799,167, in most cases, an undesirably deep penetration by the liquid-impermeable material being applied occurs. Too deep a penetration of the material forming the barrier layer is undesirable also for reasons already enumerated in the above-cited U.S. Pat. No. 3,799,167.

SUMMARY OF THE INVENTION

Starting from the above-mentioned state of the art, the problem underlying the invention is to provide an absolutely impervious and mechanically sufficiently strong liquid-impermeable layer with any desired predetermined surface stretching, while employing the smallest possible amount of material. At the same time, it should be assured in this connection that the side of the cover layer turned toward the wearer is absolutely free from the material from which the particular liquid-impermeable layer is formed. Further, the softness of the cover layer should be impaired as little as possible by the liquid-impermeable layer.

This problem is solved by that the cover layer of the disposable absorbent article of this kind is provided with a liquid-impermeable layer which consists of a heat-sealable, especially thermoplastic, material, which in the form of a prefabricated impervious sheet, penetrates with physical bonding over its entire area in any desired predetermined regions into the surface of the porous cover layer only to a small degree, without altogether penetrating this cover layer even approximately completely.

The minimized expenditure of material strived for in the formation of the liquid barrier layer is for that purpose achieved by that the barrier layer is a prefabricated sheet of an adhesive material, which is brought onto the cover layer of the disposable article solely under a light pressure over the entire surface.

While the material, on the one hand should penetrate over its entire area into the surface of the cover layer only to a small degree, in order to obtain, together with the material of the cover layer, bonding of the materials of both layers required for a sufficient strength of the barrier layer; the voids lying under the surface of the cover layer should on the other hand be filled only to the extent absolutely required for achieving a strong bond, for reasons of the least possible employment of the layer material.

In order to obtain this in the best way, the impervious sheet exhibits in its prefabricated state two differently shaped surfaces. The surface of the impervious sheet not in contact with the cover layer, which lies on the absorbent body of the disposable article is formed as smooth as possible in order to assure absolute imperviousness of the sheet even at the smallest thicknesses. The surface adjacent the surface of the cover layer, to the contrary, is best of an extremely coarse structure since this assures a physically outstanding bond between the impervious sheet and the cover layer even when the material of the impervious sheet quantitatively penetrates into the cover layer altogether only to an exceedingly small degree.

It is particularly advantageous when the impervious sheet penetrates into the cover layer only to the depth of the coarse surface. It thus is possible that for a maximum penetration of the highest peaks of about 15 to 30 $\mu$m, the depth of the penetration, averaged over the entire surface of the sheet, lies at only about 5 $\mu$m.

In this manner, impervious sheets can be employed which, especially when they consist of a material based on copolymers of alpha-olefins, exhibit surface weights of only 20 to 30 g/m$^2$, especially even only 20 to 25 g/m$^2$.

An advantageous process for the manufacture of the articles of the invention consists in that the impervious sheet with one smooth and one coarse surface is produced so that the thermoplastic, liquid-impermeable layer-forming material is applied in the molten state onto the open smooth surface of a rotating, especially cooled, roll.

In order to assure that during the application of the impervious sheet to the cover layer occurring solely under transfer pressure the material of the impervious sheet does not penetrate into the cover layer throughout the entire depth of the sheet, the impervious sheet has during its application exclusively on its surface facing the cover layer plastic deformability within a range of the thickness that is smaller than the entire thickness of the impervious sheet. The differential plastic deformability of the impervious sheet througout its thickness can be obtained during its application to the cover layer by that the temperature across the thickness of the sheet decreases in such a manner from the surface adjacent the cover layer that on the free, smooth surface of the sheet plastic deformability is no longer possible.

A process by which such a tempering of the impervious sheet during its application to the cover layer can be achieved in an exceedingly simple and economical manner consists in that a heat-sealable, especially a thermoplastic material is dispensed in a molten state onto the surface of a rotating roll whose temperature is lower than the temperature of the enviroment, and that the impervious sheet forming on the roll is brought directly from the roll with its surface not adjacent the roll upon the cover layer.

In the case of absorbent articles which are cut by the piece from continuous lengths of web material covering individual absorbent bodies spaced behind one another, and only in individual regions extending perpendicularly to the feed direction of the web material (e.g., waist closure areas of diapers) exhibit impervious sheets, which are respectively provided in a discontinuous manner, will the impervious sheet-producing heat-sealable, especially thermoplastic, material be dispensed in a molten state in a correspondingly discontinuous manner onto a rotating roll and from there as an individual impervious sheet member directly transferred onto the continuous running cover layer web material.

In the case of the liquid-impermeable layers of the invention, it is possible to reinforce in a very simple manner the physical bond between the impervious sheet and the cover layer in individual predetermined sections of the surface. Such reinforcements may be desired, e.g., in diapers in those areas to which the adhesive strips for closing the diapers on the body of the wearer are to be attached, or in the outermost edge areas of the diaper wherein the outer protective sheet is bonded to the cover layer. In the last-named case, the impervious sheet can even be employed as adhesive to achieve the desired bond. In order to obtain this or, respectively a noteworthy reinforcement of the cover layer material, the impervious sheet is made plastic in the corresponding locally limited region or, as the case may be, up to its entire depth, whereby the cover layer can be completely penetrated throughout during the application. By making the material of the impervious sheet penetrate completely throughout the cover layer, in all those places where the cover layer lies directly on the protective sheet, a common strong bond is obtainable. In this manner, e.g., the tear-off strength of the adhesive closing strips on the diapers can be considerably increased.

The zones of differential plastic deformability of the impervious sheet can be quite advantageously obtained during the production of the impervious sheet on a rotating roll and its immediate subsequent transfer onto the article being manufactured by that the regions of complete plastic deformability of the impervious sheet are produced by decreased cooling of the corresponding areas of the roll.

Irrespective of the complete penetration of the material of the impervious sheet into the regions to be reinforced of the article according to the invention, those region can also be additionally reinforced by that local thickenings of the impervious sheet can be provided. The thickenings of the impervious sheet can be predetermined, e.g., through the application of the starting material for the impervious sheet in different thicknesses onto the impervious sheet-producing rotating roll.

DETAILED DESCRIPTION OF THE DRAWINGS

Figure 1:
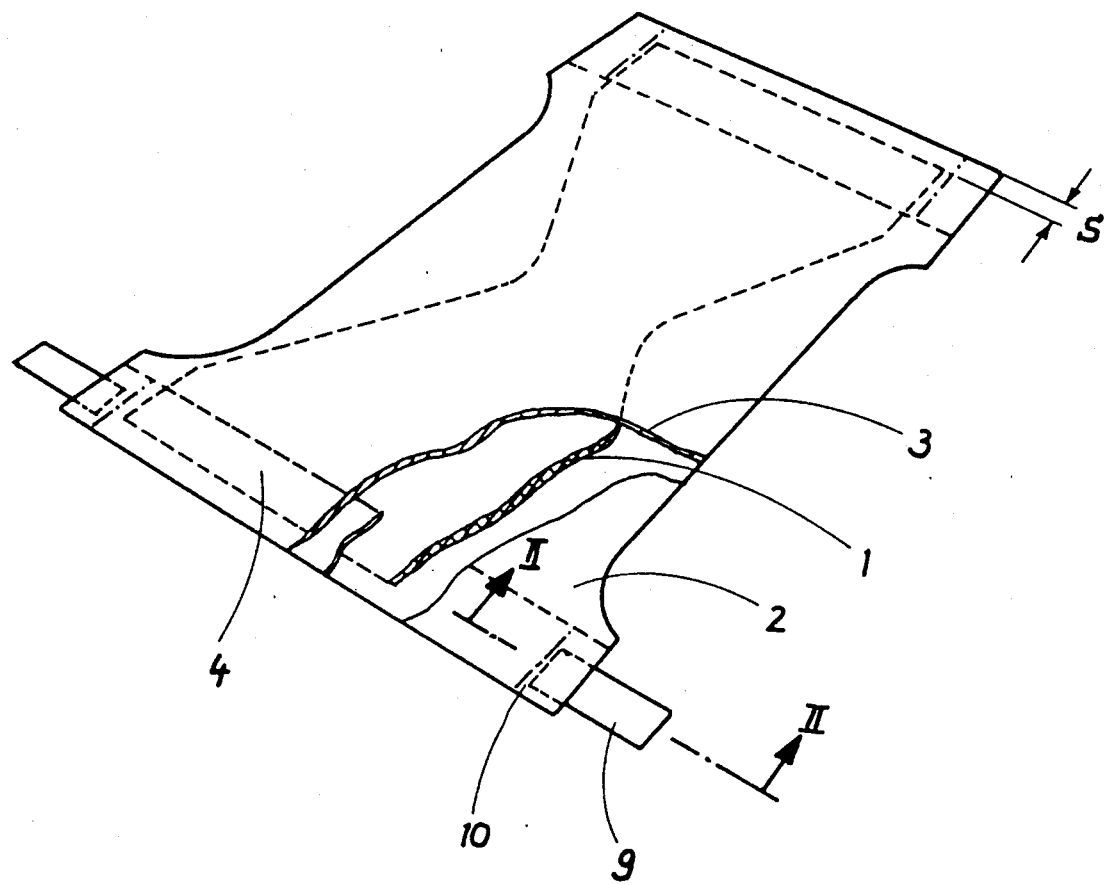
FIG. 1 is a diaper in perspective view with open edge area.
Figure 2:
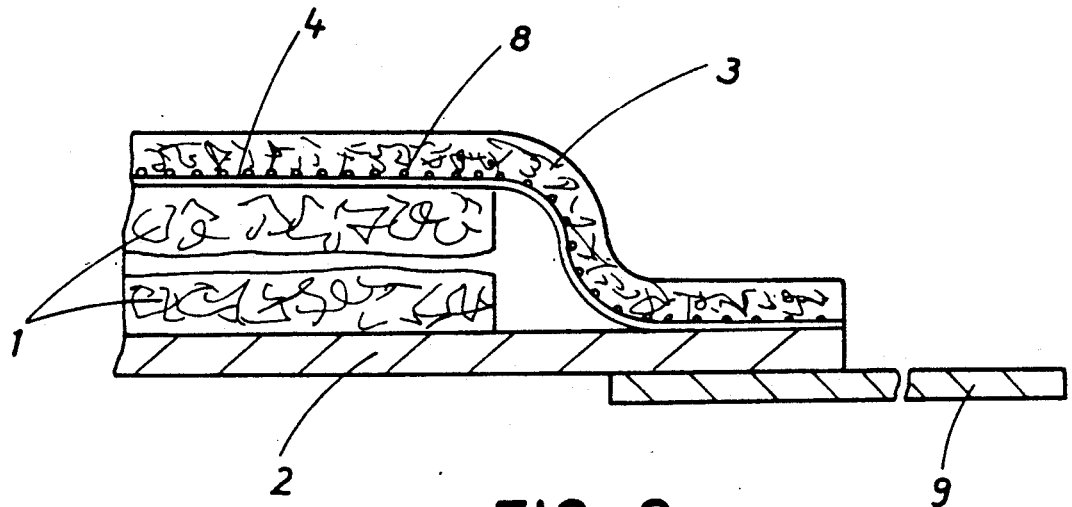
FIG. 2 is a partial cross-section along the line II—II.

While this invention is susceptible of embodiment in many different forms, there is shown in the drawings an will be herein described in detail, a specific embodiment with the understanding that the present disclosure is to be considered as an exemplification of the principles of the invention and is not intended to limit the invention to the embodiment illustrated.

A diaper consists of an absorbent material 1 which is covered on one side with a liquid-impermeable protective sheet 2 and on the other side with a fleece as porous cover layer 3. The protective sheet 2 and the cover layer 3 are glued to each other on the edges of the diaper.

In order to prevent seepage in the waist area of the diaper through the cover layer 3 of the liquid present in the porous body, there is provided in each case an impervious sheet 4 running as a strip-shaped liquid-barrier layer.

This impervious sheet 4 consists of the thermoplastic alpha-olefin copolymer material. It is applied to the cover layer 3 in a prefabricated form.

The manufacture and subsequent bringing of the impervious sheet 4 onto the cover layer 3 take place in the following manner:

The thermoplastic material forming the impervious sheet 4 is dispensed intermittently in a molten state onto a rotating cooled roll 5 with a smooth surface from a spray nozzle 6.

Figure 5:
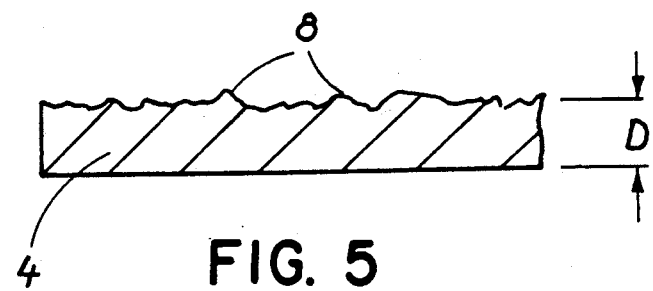
FIG. 5 is a partial cross-section through an impervious sheet along the line V—V.

The average thickness of the formed highly coarse surface of the impervious sheet facing away from the surface of the roll amounts to $D = 22$ μm (the average thickness is represented in FIG. 5). The surface weight of the impervious sheet 4 amounts to 25 g/m². Cooling of the roll 5 is so adjusted that essentially only the material lying in the coarse surface of the impervious sheet 4 still has plastic deformability while this, especially on the surface of the impervious sheet adjacent the surface of the roll, certainly no longer is the case. In this state, the individual sections of the impervious sheet 4 are transferred under only a light pressure onto the cover layer 3 fed as continuous web goods 7. The continuous web material 7 thus bonded with the impervious sheet 4 is thereafter brought upon the protective sheet 2 likewise fed as a continuous web goods, already containing the porous body 1 spaced from one another, whereby the cover layer 3 and the protective sheet 2 are bonded with each other on the edges of the diaper. The impervious sheet sections 4 which are placed at the waist-closing edges of the diaper can be employed as the adhesive material in the regions S extending in the perpendicular direction between the porous bodies 1 (FIG. 1). Bonding can proceed so that in those regions the superimposed layers are subjected to local heat sealing.

The impervious sheet 4 brought under only a light pressure onto the cover layer 3 penetrates only with the material peaks 8 into the cover layer 3. On these material peaks the physical bonding strived for is attained, which is necessary in order to assure a stable position of extremely thin sheets in the diapers. On the other hand, there always remains during the process of laying up a region of the impervious sheet that does not have plastic deformability, which is aligned on the cover layer 3 with a securely closed surface and provides for the required imperviousness.

Figure 3:
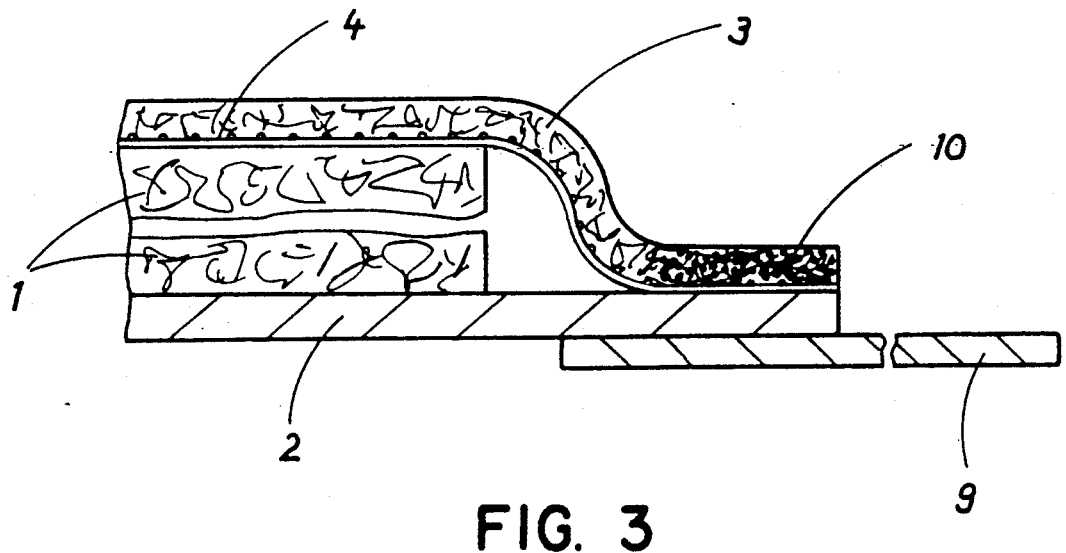
FIG. 3 is a partial cross-section of FIG. 2 with a modified attachment of the impervious sheet in the edge area of the cover layer, FIG. 4 a perspective view of a manufacturing device for the manufacture of an impervious sheet and its bringing upon a continuously fed continuous web material.

In the case when a region of the diaper within which adhesive closing strips 9 are to be attached to the impervious sheet 2 should be additionally reinforced, the impervious sheet material 4 can there be completely pressed into the cover layer material 3. This shown in FIG. 3, wherein the impervious sheet material 4 practically completely penetrates through the cover layer material 3 in the corresponding edge area 10. These edge areas 10 lying under the adhesive closing strips 9 are shown in FIG.1 with dot and dash lines.

Figure 4:
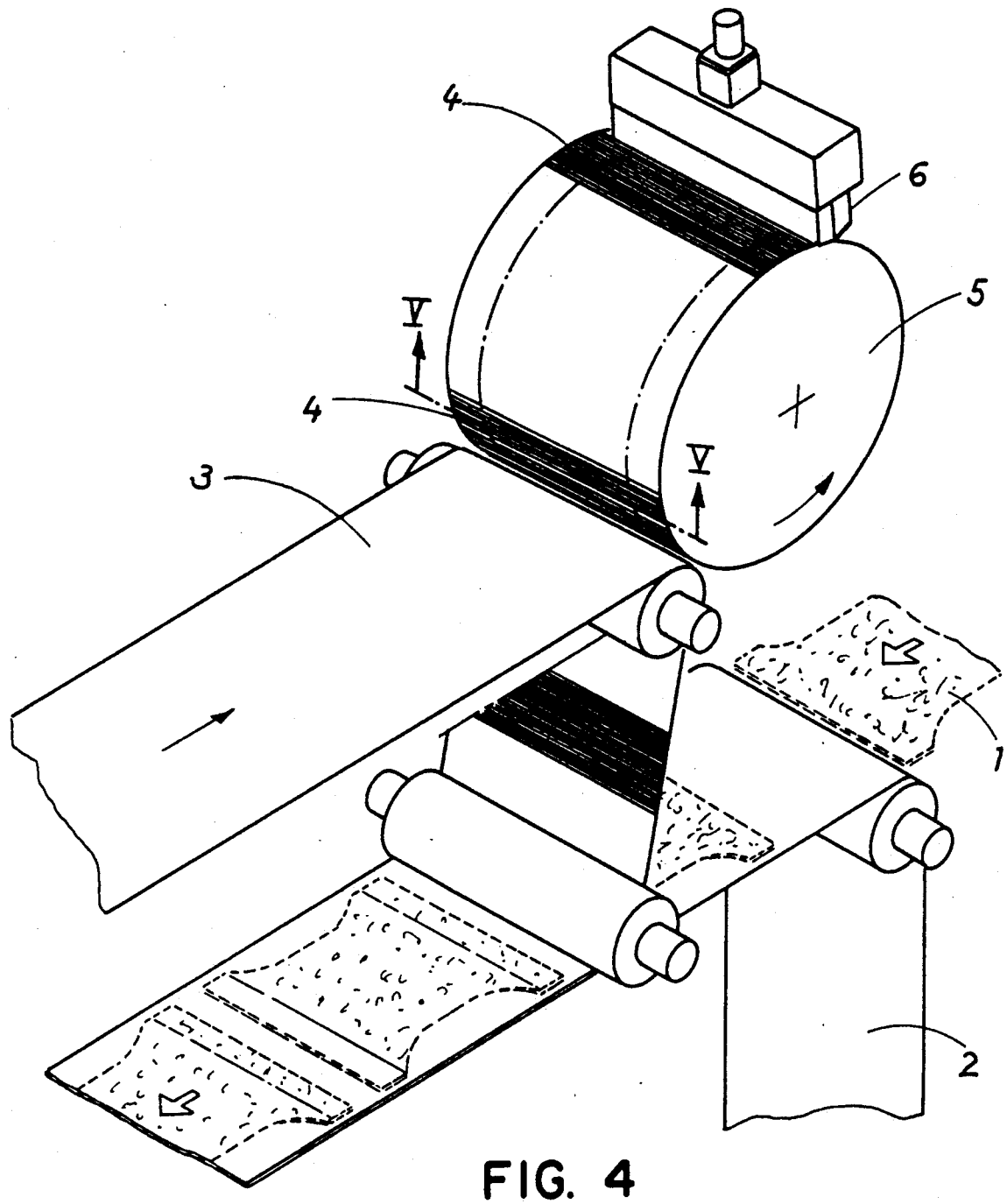

Likewise, in FIG. 4 dot and dash lines are shown on the roll 5, which there indicate those regions in the corresponding manner. The edge area extending on the roll 5 from each dot and dash line to the edge of the roll is cooled to a lesser degree when the impervious sheet should completely penetrate into the cover layer material. Because of this, the impervious sheet retains plastic deformability during the application to the cover layer over its entire depth in those regions.

If the impervious sheet is not brought directly after its formation on a rotating roll in the same process step onto the cover layer 3, it must be reheated, and indeed so that the above-described differential plastic deformability or, respectively, local nondeformability is obtained .

We claim:

1. In a process for the manufacture of an absorbent disposable article the steps comprising,
    covering a thin absorbent body having two sides on one side by a liquid-impermeable protective sheet and on a side opposite thereto by a porous cover layer, there being defined borders between the absorbent body and the porous cover layer, said absorbent body defining edges, there being defined regions where the protective sheet and the porous cover layer project beyond said edges,
    bonding the protective sheet and the porous cover layer to each other at the regions where the protective sheet and the porous cover layer project beyond said edges of the absorbent body,
    providing in at least a portion of an area near an edge of the absorbent body a liquid barrier layer so that the liquid barrier layer extends up to a respective border between the absorbent body and the porous cover layer, and wherein the liquid barrier layer is a heat-sealable thermoplastic material in the form of a liquid-impervious sheet, and
    physically bonding said liquid impervious sheet along at least one edge of said absorbent body , but only to a small extent into the surface of the porous cover layer, without however altogether penetrating the porous cover layer completely.

2. Process according to claim 1, wherein the impervious sheet has a total defined thickness, and further comprising the step of making the impervious sheet plastically deformable exclusively on a surface area thereof facing the cover layer and within a range of depth which is smaller than the total thickness of the impervious sheet.

3. Process according to claim 2, wherein the step of rendering said impervious sheet plastically deformable includes the step of varying the plastic deformability across the thickness of the impervious sheet through correspondingly variable temperature tempering of the impervious sheet so that the plastic deformability of the impervious sheet increases as the temperature increases.

4. Process according to claim 3, wherein the cover layer is initially a continous cover layer, and wherein the thermoplastic material has a softening temperature, and further comprising the step of applying the heat-sealable thermoplastic material in a molten state onto the surface of a rotating roll, so that the impervious sheet is forming on said roll,
    keeping the temperature of the rotating roll lower than the softening temperature of the thermoplastic material, and
    bringing the impervious sheet forming on the roll with a free surface thereof facing away from the roll directly from the roll onto the cover layer.

5. Process according to claim 4, further utilizing additional of said absorbent bodies lying behind one another, wherein the cover layer is a continuously unrolling cover layer, wherein a series of the disposable articles are to be produced, and further comprising the steps of
    cutting the disposable article from a continuous web material having a predetermined feed direction,
    dispensing the thermoplastic material sheet in a molten state in a discontinuous manner the rotating roll, so as to form respective individual impervious sheets,
    transferring each so formed individual impervious sheet from said rotating roll directly onto the continuously running cover layer,
    covering individual of said absorbent bodies lying behind one another at intervals with respective portions of said cover layer, and
    applying said impervious sheets only at respective individual areas of a respective absorbent body transversely to the feed direction of the web material.

6. In a process according to claim 1, wherein adhesive closure strips are provided for closing the absorbable article, said adhesive strips being arranged to engage a person, and further comprising the step of causing the impervious sheet to penetrate completely into the porous cover layer and forming a physical bond with the protective sheet only in locally limited areas of the protective sheet in which said adhesive closure strips for closing the absorbable article are arranged to engage the person.

7. In a process according to claim 1, further comprising the steps of rendering the impervious sheet completely plastically deformable while being applied to the the cover layer in a predetermined region, and causing the impervious sheet to enter into a physical bond with the respective sheet in said predetermined region.

8. Process according to claim 7, wherein subsequent to the step of producing the impervious sheet on the rotating cooled roll, and subsequent to the direct transfer of the impervious sheet onto the unrolling cover layer the process includes the further step of producing regions of full plastic deformability of the impervious sheet by decreased cooling of corresponding regions of the roll.

9. Process according to claim 6, wherein the adhesive strips has gripping areas which are thicker than remaining areas thereof, and further comprising the step of applying the material of the impervious sheet in said gripping areas of the adhesive strips.

10. Process according to claim 9, wherein the step of applying the molten heat-sealable and thermoplastic material onto the roll further includes the step of producing the impervious sheet in variable respective thicknesses.

* * * * *

UNITED STATES PATENT AND TRADEMARK OFFICE
CERTIFICATE OF CORRECTION

PATENT NO. : 5,013,382

DATED : May 7, 1991

INVENTOR(S) : Krzysztof Malowaniec, Kurt Simmler

It is certified that error appears in the above-identified patent and that said Letters Patent is hereby corrected as shown below:

On the title page:

ITEM [75]   Should read -- Krzysztof Malowaniec; Kurt Simmler, both of Heidenheim, Fed. Rep. of Germany --.

Col. 1, Line 10   Between "in" and "particular", delete "a".

Col. 1, Line 27   Delete "inprinciple" and insert instead -- in principle --.

Col. 6, Line 53   Between "manner" and "the", insert -- onto --.

Signed and Sealed this

Thirty-first Day of December, 1991

Attest:

HARRY F. MANBECK, JR.

Attesting Officer    Commissioner of Patents and Trademarks